(12) United States Patent
Wulfman et al.

(10) Patent No.: US 11,660,379 B2
(45) Date of Patent: May 30, 2023

(54) DURABLE ANTIMICROBIAL LAYER FOR IMPLANTABLE MEDICAL DEVICES

(71) Applicant: Cardiac Pacemakers, Inc., St. Paul, MN (US)

(72) Inventors: David R. Wulfman, Minneapolis, MN (US); Danielle Frankson, Dayton, MN (US); Adeniyi O. Aremu, Brooklyn Park, MN (US); Angelo Fruci, Mahtomedi, MN (US); Gregory J. Sherwood, North Oaks, MN (US); Mary M. Byron, Roseville, MN (US); Joseph T. Delaney, Jr., Minneapolis, MN (US); Adam McGraw, Mansfield, MA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 17/701,421

(22) Filed: Mar. 22, 2022

(65) Prior Publication Data

US 2022/0211919 A1    Jul. 7, 2022

Related U.S. Application Data

(62) Division of application No. 15/672,674, filed on Aug. 9, 2017, now Pat. No. 11,324,860.

(Continued)

(51) Int. Cl.
*A61L 24/00* (2006.01)
*B05D 3/00* (2006.01)
(Continued)

(52) U.S. Cl.
CPC .......... *A61L 29/16* (2013.01); *A61F 2/30767* (2013.01); *A61L 27/28* (2013.01);
(Continued)

(58) Field of Classification Search
CPC .................................................. A61L 2420/02
See application file for complete search history.

(56) References Cited

U.S. PATENT DOCUMENTS

| 6,451,003 B1 | 9/2002 | Prosl et al. |
| 7,322,965 B2 | 1/2008 | Gibson et al. |

(Continued)

FOREIGN PATENT DOCUMENTS

| WO | 93/07924 A1 | 4/1993 |
| WO | 2005/084582 A1 | 9/2005 |
| WO | 2007/078304 A2 | 7/2007 |

OTHER PUBLICATIONS

Agarwal, Seema, et al. "Use of Electrospinning Technique for Biomedical Applications." Polymer, 49:5603-5621, 2008.

(Continued)

*Primary Examiner* — Cachet I Proctor
(74) *Attorney, Agent, or Firm* — Nelson Mullins Riley & Scarborough LLP (57) ABSTRACT

An implantable medical device includes a polymer substrate and at least one nanofiber. The polymer substrate includes a surface portion extending into the polymer substrate from a surface of the substrate. The at least one nanofiber includes a first portion and a second portion. The first portion is interpenetrated with the surface portion of the substrate, and mechanically fixed to the substrate. The second portion projects from the surface of the substrate.

11 Claims, 6 Drawing Sheets

Related U.S. Application Data (60) Provisional application No. 62/372,416, filed on Aug. 9, 2016.

(51) Int. Cl.

| | | |
|---|---|---|
| *A61L 29/16* | (2006.01) | |
| *A61L 31/06* | (2006.01) | |
| *A61L 31/04* | (2006.01) | |
| *A61L 31/10* | (2006.01) | |
| *B05D 3/06* | (2006.01) | |
| *B05D 3/10* | (2006.01) | |
| *A61F 2/30* | (2006.01) | |
| *A61L 27/28* | (2006.01) | |
| *B05D 3/02* | (2006.01) | |

(52) U.S. Cl.
CPC ............ *A61L 31/046* (2013.01); *A61L 31/06* (2013.01); *A61L 31/10* (2013.01); *B05D 3/007* (2013.01); *B05D 3/061* (2013.01); *B05D 3/108* (2013.01); *A61F 2002/30677* (2013.01); *A61L 2300/606* (2013.01); *A61L 2400/12* (2013.01); *A61L 2420/02* (2013.01); *A61M 2207/00* (2013.01); *B05D 3/0254* (2013.01); *B05D 2518/00* (2013.01)

(56) References Cited

U.S. PATENT DOCUMENTS

| | | |
|---|---|---|
| 8,685,424 B2 | 4/2014 | Ballard et al. |
| 8,889,572 B2 | 11/2014 | Scrivens et al. |
| 9,090,995 B2 | 7/2015 | Imashiro et al. |
| 11,324,860 B2 | 5/2022 | Wulfman et al. |
| 2006/0204738 A1* | 9/2006 | Dubrow ................. A61F 13/02 428/292.1 |
| 2006/0275283 A1 | 12/2006 | Van et al. |
| 2007/0190880 A1 | 8/2007 | Dubrow et al. |
| 2007/0282247 A1* | 12/2007 | Desai ..................... A61L 27/54 604/19 |
| 2008/0157444 A1* | 7/2008 | Melsheimer ......... D01D 5/0076 264/514 |
| 2009/0020921 A1* | 1/2009 | Cakmak ................... B32B 5/30 264/172.19 |
| 2010/0120315 A1 | 5/2010 | Imashiro et al. |
| 2010/0292791 A1 | 11/2010 | Lu et al. |
| 2011/0201984 A1* | 8/2011 | Dubrow ................. A61L 31/10 602/54 |
| 2013/0053948 A1 | 2/2013 | Anneaux et al. |
| 2015/0202423 A1 | 7/2015 | Adenusi et al. |
| 2018/0043064 A1 | 2/2018 | Wulfman et al. |

OTHER PUBLICATIONS

H1465, Implantable Lead Infection Barrier, Jul. 4, 1995, Stokes, et al., 4 pages.

Huang, Zheng-Ming et al., "A review on polymer nanofibers by electrospinning and their applications in nanocomposites", Composites Science and Technology, No. 66, 2003, pp. 2223-2253.

International Search Report and Written Opinion issued in PCT/US2017/046050, dated Oct. 26, 2017, 13 pages.

Reddy, Shravanthi T., et al. "Micropatterned Surfaces for Reducing the Risk of Catheter-Associated Urinary Tract Infection: An In Vitro Study on the Effect of Sharklet Micropatterned Surfaces to Inhibit Bacterial Colonization and Migration of Uropathogenic *Escherichia coli*." Journal of Endourology, 25(9):154 7-1552, Sep. 2011.

Scardino, Andrew J. "Mini Review: Biomimetic Models and Bioinspired for Fouling Control," Biofouling, 27(1):73-86, Jan. 2011.

* cited by examiner

DURABLE ANTIMICROBIAL LAYER FOR IMPLANTABLE MEDICAL DEVICES

CROSS-REFERENCE TO RELATED APPLICATION

This application is a divisional application that claims priority to U.S. application Ser. No. 15/672,674, filed Aug. 9, 2017, which claims priority to Provisional Application No. 62/372,416, filed Aug. 9, 2016, which are herein incorporated by reference in its entirety.

TECHNICAL FIELD

The present invention relates to preventing infections associated with implantable medical devices. More specifically, the invention relates to antimicrobial, antifouling layers and methods for forming antimicrobial, antifouling layers on surfaces of implantable medical devices.

BACKGROUND

Implantable medical devices may include a housing and a lead or catheter for delivering therapy to a treatment site within a patient's body. For example, a cardiac rhythm management system may include a housing, or pulse generator, containing electronics and a battery; and an electrical lead extending from the pulse generator to a treatment site—the heart. In another example, a drug delivery system may include a housing, or drug delivery pump, containing the pump, a battery, and a supply of the drug; and a catheter extending from the drug delivery pump to the treatment site requiring the drug. In some cases, the housing may be installed in a subcutaneous pocket within a patient's body.

Implanting a medical device within a patient inherently exposes the patient to a risk of a nosocomial (e.g., hospital-acquired) infection associated with bacteria adhering to the exterior of the medical device. For example, the average nosocomial infection rate associated with the implantation of cardiovascular implantable electronic devices in 2008 was approximately 2.4 percent. In some cases of infection, the implantable medical device, including a device housing and any associated electrical leads or catheters, must be completely removed. Following removal, the infection must be cured and the patient must heal enough to tolerate implantation of a replacement medical device. The costs of such infections are significant, averaging about $146,000 per infection. The physical and emotional stress suffered by the patient may represent an even more significant cost.

What is needed is a way to reduce the occurrence of infections which may result from implanting a medical device within a patient.

SUMMARY

Example 1 is an implantable medical device including a polymer substrate and at least one nanofiber. The polymer substrate includes a surface portion extending into the polymer substrate from a surface of the substrate. The at least one nanofiber includes a first portion and a second portion. The first portion is interpenetrated with the surface portion of the substrate, and mechanically fixed to the substrate. The second portion projects from the surface of the substrate Example 2 is the implantable medical device of Example 1, wherein the at least one nanofiber has an average diameter ranging from about 100 nanometers to about 1,000 nanometers.

Example 3 is the implantable medical device of either of Examples 1 or 2, further including a plurality of the nanofibers, wherein at least some of the plurality of nanofibers includes the first portion and the second portion.

Example 4 is the implantable medical device of any of Examples 1-3, wherein the at least one nanofiber includes at least one of a fluoropolymer or a polyurethane.

Example 5 is the implantable medical device of Example 4, wherein the at least one nanofiber further includes poly (ethylene glycol).

Example 6 is the implantable medical device of any of Examples 1-5, further including a cross-linked poly(ethylene glycol) coating mechanically linked to the second portion of the at least one nanofiber.

Example 7 is the implantable medical device of Example 6, wherein the cross-linked poly(ethylene glycol) coating includes an initiator residue.

Example 8 is the implantable medical device of either of Examples 6 or 7, wherein the cross-linked poly(ethylene glycol) coating is bonded to the second portion of the at least one nanofiber by covalent bonds.

Example 9 is a method of forming an antimicrobial layer on a surface of a polymer substrate of an implantable medical device. The method includes interpenetrating a first portion of at least one nanofiber within a surface portion of the substrate, the surface portion extending from the surface into the substrate, the surface portion being in a liquid or semi-liquid state; and solidifying the surface portion, wherein the first portion of the at least one nanofiber is mechanically fixed within the surface portion and a second portion of the at least one nanofiber projects away from the surface.

Example 10 is the method of Example 9, wherein interpenetrating the first portion of the at least one nanofiber within the surface portion includes electro-spinning a nanofiber directly into the surface portion.

Example 11 is the method of Example 9, wherein interpenetrating the first portion of the at least one nanofiber within the surface portion includes electro-spinning the at least one nanofiber onto a core pin or a mandrel and over-molding the surface portion onto the first portion of the at least one nanofiber on the core pin or mandrel.

Example 12 is the method of any of Examples 9-11, wherein solidifying the surface portion includes cross-linking the polymer substrate around the first portion of the at least one nanofiber.

Example 13 is the method of any of Examples 9-12, further including coating the second portion of the at least one nanofiber with a poly(ethylene glycol) and cross-linking the poly(ethylene glycol) coating to mechanically link the poly(ethylene glycol) to the second portion of the at least one nanofiber.

Example 14 is the method of Example 13, wherein the poly(ethylene glycol) includes at least one of an ultraviolet initiator and a thermal initiator, and cross-linking the poly (ethylene glycol) coating includes exposing the ultraviolet initiator and the thermal initiator to ultraviolet radiation or heat, respectively.

Example 15 is the method of either of Examples 13-14, further including exposing the second portion of the plurality of nanofibers and the poly(ethylene glycol) coating to an argon-containing plasma to covalently bond the cross-linked poly(ethylene glycol) coating to the second portion of the plurality of nanofibers.

Example 16 is an implantable medical device including a polymer substrate and at least one nanofiber. The polymer substrate includes a surface portion extending into the polymer substrate from a surface of the substrate. The at least one nanofiber includes a first portion and a second portion. The first portion is interpenetrated with the surface portion of the substrate, and mechanically fixed to the substrate. The second portion projects from the surface and forms an antimicrobial layer on the surface.

Example 17 is the implantable medical device of Example 16, wherein the at least one nanofiber has an average diameter ranging from about 100 nanometers to about 1,000 nanometers.

Example 18 is the implantable medical device of either of Examples 16 or 17, further including a plurality of the nanofibers, wherein at least some of the plurality of nanofibers includes the first portion and the second portion.

Example 19 is the implantable medical device of any of Examples 16-18, wherein the at least one nanofiber includes at least one of a fluoropolymer or a polyurethane.

Example 20 is the implantable medical device of any of Examples 16-18, wherein the at least one nanofiber further includes poly(ethylene glycol).

Example 21 is the implantable medical device of any of Examples 16-20, further including a cross-linked poly(ethylene glycol) coating mechanically linked to the second portion of the at least one nanofiber.

Example 22 is the implantable medical device of Example 21, wherein the cross-linked poly(ethylene glycol) coating includes an initiator residue.

Example 23 is the implantable medical device of either of Examples 21 or 22, wherein the cross-linked poly(ethylene glycol) coating is bonded to the second portion of the at least one nanofiber by covalent bonds.

Example 24 is an implantable medical device including a polymer substrate and a plurality of nanofibers. The polymer substrate includes a surface and a surface portion extending from the surface to a depth into the polymer substrate. The plurality of nanofibers include a first portion and a second portion. The first portion is interpenetrated with the surface portion of the substrate, and mechanically fixed to the substrate. The second portion projects from the surface and forms an antimicrobial layer on the surface.

Example 25 is the implantable medical device of Example 24, wherein the nanofibers have diameters ranging from about 100 nanometers to about 1,000 nanometers.

Example 26 is the implantable medical device of either of Examples 24 or 25, further including a cross-linked poly(ethylene glycol) coating mechanically linked to the second portion.

Example 27 is the implantable medical device of Example 26, wherein the cross-linked poly(ethylene glycol) coating includes an initiator residue.

Example 28 is the implantable medical device of either of Examples 26 or 27, wherein the cross-linked poly(ethylene glycol) coating is bonded to the second portion by covalent bonds.

Example 29 is a method of forming an antimicrobial layer on a surface of a polymer substrate of an implantable medical device. The method includes interpenetrating a first portion of at least one nanofiber within a surface portion of the substrate, the surface portion extending from the surface into the substrate, the surface portion being in a liquid or semi-liquid state; and solidifying the surface portion, wherein the first portion of the at least one nanofiber is mechanically fixed within the surface portion and a second portion of the at least one nanofiber projects away from the surface to form the antimicrobial layer.

Example 30 is the method of Example 29, wherein interpenetrating the first portion of the at least one nanofiber within the surface portion includes electro-spinning a nanofiber directly into the surface portion.

Example 31 is the method of Example 29, wherein interpenetrating the first portion of the at least one nanofiber within the surface portion includes electro-spinning the at least one nanofiber onto a core pin or a mandrel and over-molding the surface portion onto the first portion of the at least one nanofiber on the core pin or mandrel.

Example 32 is the method of any of Examples 29-31, wherein solidifying the surface portion includes cross-linking the polymer substrate around the first portion of the at least one nanofiber.

Example 33 is the method of any of Examples 29-32, further including coating the second portion of the at least one nanofiber with a poly(ethylene glycol) and cross-linking the poly(ethylene glycol) coating to mechanically link the poly(ethylene glycol) to the second portion of the at least one nanofiber.

Example 34 is the method of Example 33, wherein the poly(ethylene glycol) includes at least one of an ultraviolet initiator and a thermal initiator, and cross-linking the poly(ethylene glycol) coating includes exposing the ultraviolet initiator and the thermal initiator to ultraviolet radiation or heat, respectively.

Example 35 is the method of either of Examples 33 or 34, further including exposing the second portion of the plurality of nanofibers and the poly(ethylene glycol) coating to an argon-containing plasma to covalently bond the cross-linked poly(ethylene glycol) coating to the second portion of the plurality of nanofibers.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention. The detailed description of the invention which follows is intended to illustrate but not limit the invention.

In accordance with various aspects of the disclosure, a medical device is defined as "an implantable medical device" if it is totally or partly introduced, surgically or medically, into the human body or by medical intervention into a natural orifice, and which is intended to remain after the procedure. Exemplary implantable medical devices can include a medical electrical lead or a suture sleeve, as discussed below. However, it is understood that the various embodiments can be implemented in any implantable medical device implanted in a patient. For example, embodiments may be employed with a subcutaneously-implanted implantable cardioverter-defibrillator (ICD) housing and lead system. Such a system may include a housing implanted in a subcutaneous pocket in a patient's chest, and a lead traversing a subcutaneous path from the subcutaneous pocket to the anterior precordial region. Embodiments may be employed within the subcutaneous pocket containing the ICD housing and along the subcutaneous path traversed by the lead. Other such implantable medical devices include, without limitation, cardioverter-defibrillator or cardiac resynchronization therapy devices, leadless pacing devices, implantable cardiac monitors, endocardial leads, epicardial leads, neurostimulation systems such as spinal cord stimulation or deep brain stimulation device housings and associated leads, implantable drug pumps, ostomy ports, and urology catheters, to name a few.

Figure 1:
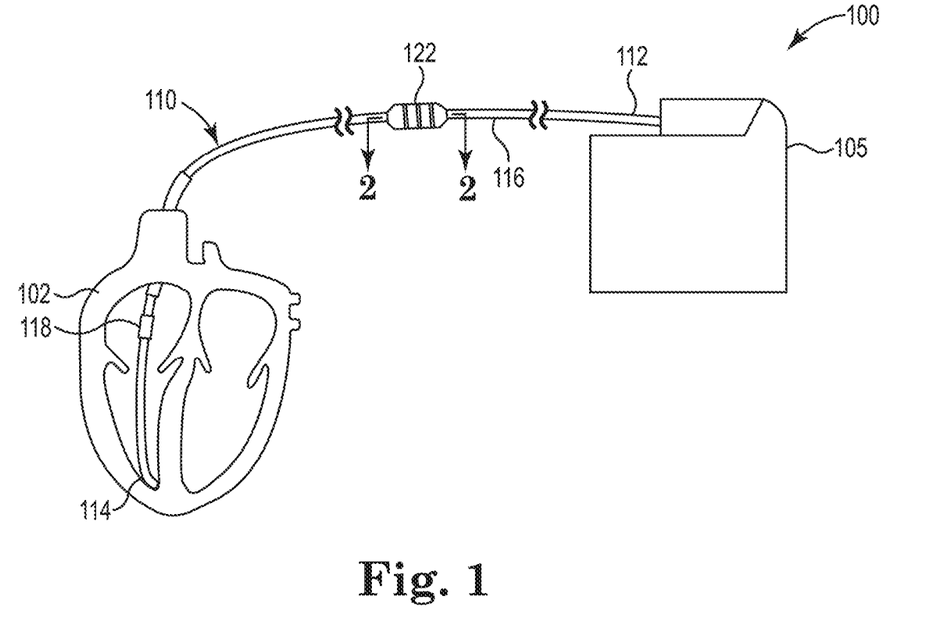
FIG. 1 is a schematic illustration of exemplary implantable medical devices including a medical electrical lead and a suture sleeve.

FIG. 1 is a schematic illustration of exemplary implantable medical devices including a medical electrical lead 110 and a suture sleeve 122. FIG. 1 shows a cardiac rhythm management (CRM) system 100 for delivering and/or receiving electrical pulses or signals to stimulate, shock, and/or sense a heart 102. The CRM system 100 can include a pulse generator 105 and the medical electrical lead 110. The pulse generator 105 includes a source of power as well as an electronic circuitry portion. The pulse generator 105 may be a battery-powered device which generates a series of timed electrical discharges or pulses. The pulse generator 105 may be implanted into a subcutaneous pocket made in the wall of the chest. Alternatively, the pulse generator 105 may be placed in a subcutaneous pocket made in the abdomen, or in another location. It should be noted that while the medical electrical lead 110 is illustrated for use with a heart 102, the medical electrical lead 110 is suitable for other forms of electrical stimulation/sensing as well.

In some embodiments, the medical electrical lead 110 extends from a proximal end 112, where it is coupled with the pulse generator 105 to a distal end 114, which is coupled with a portion of the heart 102, when implanted or otherwise coupled therewith. The medical electrical lead 110 includes a lead body 116 extending generally from the proximal end 112 to the distal end 114. The lead body 116 may be a tubular structure. Disposed along a portion of the medical electrical lead 110, for example near the distal end 114, may be at least one electrode 118 which electrically couples the medical electrical lead 110 with the heart 102. At least one electrical conductor 120 (FIG. 2) may be disposed within the lead body 116 and extend generally from the proximal end 112 to the distal end 114. The at least one electrical conductor 120 electrically connects the electrode 118 with the proximal end 112 of the medical electrical lead 110 to couple the electrode 118 to the pulse generator 105. The electrical conductor 120 carries electrical current and pulses between the pulse generator 105 and the electrode 118, and to and from the heart 102.

The medical electrical lead 110 can be secured in place by the suture sleeve 122. Migration and dislodgment of the medical electrical lead 110 may be discouraged by securing the suture sleeve 122 about the lead body 116 and suturing the suture sleeve 122 to the patient's tissue.

Figure 2:
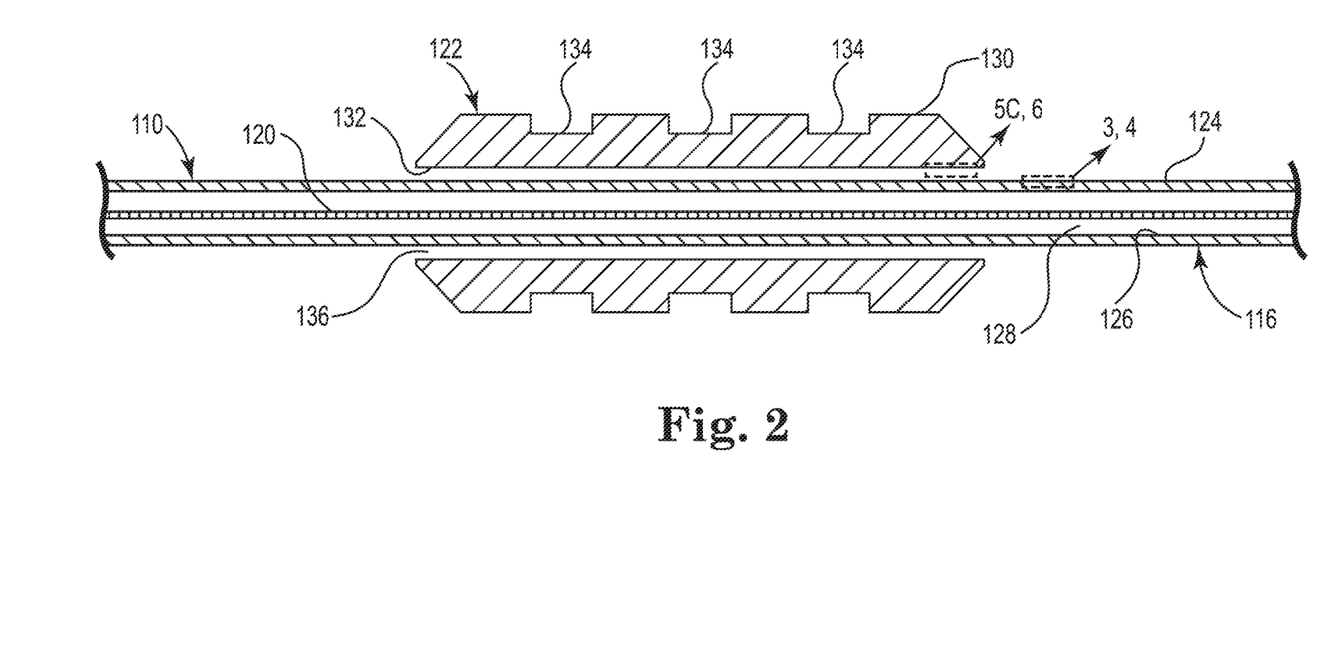
FIG. 2 is a schematic cross-sectional view of a portion of the implantable medical electrical lead FIG. 1.

FIG. 2 is a schematic cross-sectional view of a portion of the implantable medical electrical lead 110 of FIG. 1 showing the suture sleeve 122 about the lead body 116. In the embodiment shown in FIG. 2, the lead body 116 is a tubular structure including an outer surface 124, and an inner surface 126. The inner surface 126 defines a lead lumen 128. The electrical conductor 120 extends through the lead lumen 128 from the proximal end 112 to the electrode 118 (FIG. 1). The suture sleeve 122 includes an outer surface 130 and an inner surface 132. In the embodiment of FIG. 2, the suture sleeve 122 also includes at least one suture groove 134 (three shown) in the outer surface 130 extending around the circumference of the suture sleeve 122. The inner surface 132 defines a suture sleeve lumen 136 extending the length of the suture sleeve 122. A diameter of the suture sleeve lumen 136 is greater than a diameter of the lead body 116 such that the suture sleeve lumen 136 may be moved along the lead body 116 to a position adjacent to tissue suitable for attachment. Once the suture sleeve lumen 136 is positioned adjacent to tissue, sutures (not shown) may be tightly wrapped around the suture sleeve 122 in the suture grooves 134 and sutured to the patient's tissue. The tightly wrapped sutures in the suture grooves 134 can compress the inner surface 132 of the suture sleeve 122 adjacent to the suture grooves 134 against the outer surface 124 of the lead body 116, securing the lead body 116 within the suture sleeve 122.

The lead body 116 and the suture sleeve 122 include any suitable biostable, biocompatible polymer, such as a silicone or a polyurethane. The lead body 116 can be formed by extruding or by molding. The suture sleeve 122 can also be formed by molding. The lead body 116 and the suture sleeve 122 are exemplary polymer substrates.

The outer surface 124 of the lead body 116 can include various marks and surface features (not shown). For example, lead bodies may be extruded and the extrusion process may produce marks and surface features. It has been found that the marks and surface features may provide a safe haven for bacteria to colonize the surface of the lead body 116, leading to pocket infections, bacteremia, or endocarditis. Similarly, the outer surface 130 and the inner surface 132 of the suture sleeve 122 can also include various marks and surface features suitable for the colonization of bacteria. Bacteria growth can be particularly aggressive on the outer surface 124 of lead body 116 under the edge of the suture sleeve 122 in suture sleeve lumen 136.

Figure 3:
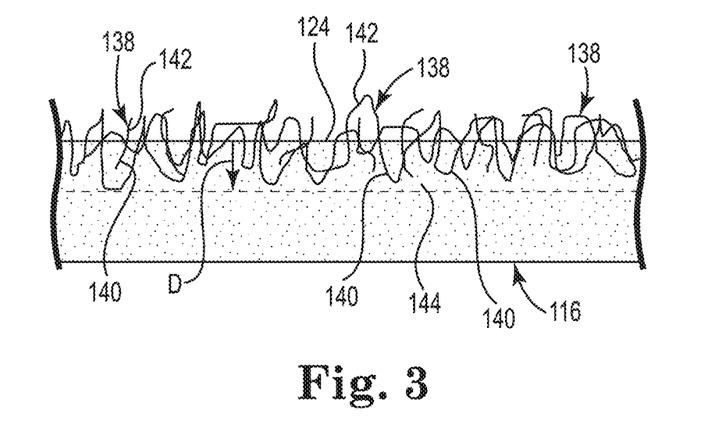
FIG. 3 is an enlarged schematic cross-sectional view of a portion of the lead body 116 of FIG. 2 illustrating an antimicrobial layer on an outer surface of a medical electrical lead, according to some embodiments.

FIG. 3 is an enlarged schematic cross-sectional view of a portion of the lead body 116 of FIG. 2 illustrating an antimicrobial layer on the outer surface 124 of a medical electrical lead 110, according to some embodiments. As shown in FIG. 3, the lead body 116 includes at least one nanofiber 138. The nanofiber 138 includes a first portion 140 and a second portion 142. The first portion 140 is embedded in, or interpenetrated with, a surface portion 144 of the lead body 116. The surface portion 144 extends from the outer surface 124 into the lead body 116 to a depth D. The second portion 142 projects from the outer surface 124. The first portion 140 is mechanically fixed to the outer surface 124 by virtue of the embedded, interpenetrating structure. It has been found that the second portion 142 of the nanofiber 138 projecting from the outer surface 124 presents a surface morphology that is less amenable for bacterial adhesion than the outer surface 124 without the nanofiber 138. By discouraging adhesion of bacteria to the outer surface 124, the second portion 142 forms an antimicrobial layer that may inhibit bacterial colonization. The antimicrobial layer formed by the second portion 142 is durable because the nanofiber 138 is mechanically fixed to the surface portion 144 by the first portion 140.

In some embodiments, the nanofiber 138 winds its way into and out of the surface portion 144 to define the first portion 140 and the second portion 142. Such a structure can produce loops of nanofibers embedded in the surface portion 144 which may help mechanically fix the first portion 140 to the surface portion 144. In the embodiment shown in FIG. 3, the at least one nanofiber 138 includes a plurality of nanofibers 138, winding their way into and out of the surface portion 144 with their own first portions 140 interpenetrated with the surface portion 144, and second portions 142 projecting form the outer surface 124.

In some embodiments, the depth D to which the surface portion 144 extends may be as small as about 10 microns, about 20 microns, or about 30 microns, or as great as about 50 microns, about 60 microns, or about 125 microns, or may extend an amount within any range defined between any pair of the foregoing values. In some embodiments, the depth D may range from about 10 microns to about 125 microns, about 20 microns to about 60 microns, or about 30 microns to about 50 microns. In some embodiments, the depth D may be about 40 microns.

In some embodiments, the at least one nanofiber 138 can have an average diameter as small as about 100 nanometers, about 200 nanometers, or about 400 nanometers, or as large as about 600 nanometers, about 800 nanometers, or about 1,000 nanometers. In some embodiments, the average diameter of the at least one nanofiber 138 can range from about 100 nanometers to about 1,000 nanometers, about 200 nanometers to about 800 nanometers, or about 400 nanometers to about 600 nanometers. In some embodiments, the at least one nanofiber 138 can have a diameter of about 500 nanometers. In embodiments in which the at least one nanofiber 138 includes a plurality of nanofibers 138, the nanofiber diameter size may be determined by measuring the average diameter of the nanofibers.

The at least one nanofiber 138 may include any suitable biostable, biocompatible polymer that can be formed into nanofibers. In some embodiments in which the nanofiber 138 is formed by electro-spinning, the nanofiber 138 can include a fluoropolymer, such as polytetrafluoroethylene (PTFE), polyvinlyidene fluoride (PVDF), or poly(vinylidene fluoride-co-hexafluoropropene) (PVDF-HPV); a polyurethane, such as polyether polyurethane, polycarbonate polyurethane, or polyisobutylene-polyurethane (PIB-PUR); or styrene-isobutylene-styrene (SIBS).

In some embodiments, the at least one nanofiber 138 can include a suitable hydrophilic polymer, such as poly(ethylene glycol), blended with the nanofiber polymer (e.g., the fluoropolymer, the polyurethane, or the SIBS). That is, the nanofiber 138 may be formed from a blend of the nanofiber polymer and poly(ethylene glycol). In such embodiments, exposing the nanofiber 138 to a plasma that contains argon can cross-link the poly(ethylene glycol) and covalently bond the poly(ethylene glycol) to the nanofiber polymer, as described below in reference to FIG. 4. The poly(ethylene glycol) in the nanofiber 138 is cross-linked so that it is biostable, and is covalently bonded to the nanofiber polymer so that it is durably attached to the nanofiber polymer to form the nanofiber 138. The presence of the cross-linked poly(ethylene glycol) in the nanofiber 138 may further discourage bacterial adhesion by making the nanofiber 138 hydrophilic, increasing the antimicrobial, anti-fouling effect of the second portion 142.

In some embodiments, the antimicrobial layer is formed on the outer surface 124 of the lead body 116 by interpenetrating the first portion 140 of the at least one nanofiber 138 within the surface portion 144 while the surface portion 144 is in a liquid or semi-liquid state, and then solidifying the surface portion 144 with the second portion 142 projecting away from the outer surface 124. In some embodiments in which the lead body 116 is made of a thermoset polymer, such as a silicone, the nanofiber 138 can interpenetrate the surface portion 144 while the polymer is in a liquid or semi-liquid state before it solidifies by curing, or cross-linking portions of the polymer around portions of the first portion 140. In other embodiments in which the lead body 116 is made of a thermoplastic polymer, the nanofiber 138 can interpenetrate the surface portion 144 while the polymer is in a liquid or semi-liquid state created by heating the polymer to melt or soften the surface portion 144, or by dissolution of the surface portion 144 in a suitable solvent. For example, when the lead body 116 is formed of a polyurethane, tetrahydrofuran or dimethylformamide may be used to soften the surface portion 144, creating a semi-liquid state. Once the first portion 140 of the nanofiber 138 has interpenetrated the surface portion 144, the surface portion 144 can be cooled, or the solvent permitted to evaporate, to solidify the surface portion 144, mechanically fixing the first portion 140 within the surface portion 144.

In some embodiments, interpenetration the first portion 140 of the nanofiber 138 within the surface portion 144 includes electro-spinning a nanofiber directly into the surface portion 144 while the surface portion 144 is in a liquid or semi-liquid state.

Figure 4:
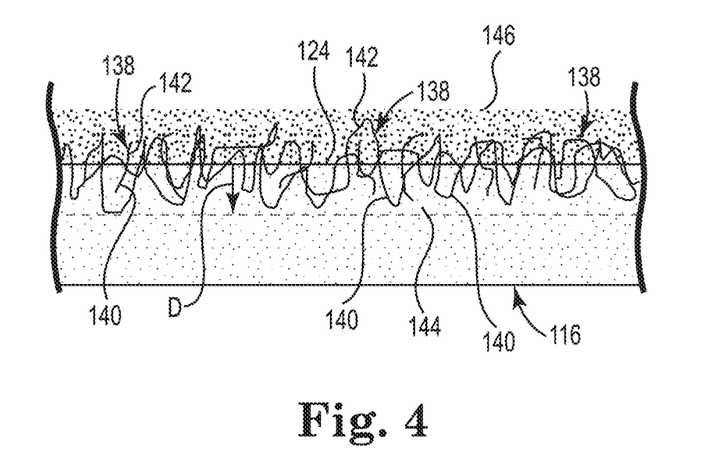
FIG. 4 is an enlarged schematic cross-sectional view of a portion of the lead body 116 of FIG. 2 illustrating an antimicrobial layer on an outer surface of a medical electrical lead, according to some embodiments.

FIG. 4 is an enlarged schematic cross-sectional view of a portion of the lead body 116 of FIG. 2 illustrating an antimicrobial layer on the outer surface 124 of a medical electrical lead 110, according to some embodiments. The embodiment shown in FIG. 4 is similar or identical to the embodiment shown in FIG. 3, except that it includes a cross-linked poly(ethylene glycol) coating 146 on the second portion 142. The poly(ethylene glycol) coating 146 is cross-linked around and between at least some of the second portion 142 so that it is mechanically linked to the at least one nanofiber 138. The poly(ethylene glycol) coating 146 is also biostable because it is cross-linked. The presence of the poly(ethylene glycol) coating 146 around the nanofibers 138 may further discourage bacterial adhesion by providing a hydrophilic, anti-fouling coating on the second portion 142 of the nanofibers 138. It has been found that the combination of the surface morphology of the second portion 142 and the hydrophilic, cross-linked poly(ethylene glycol) coating 146 provides a durable, antimicrobial, anti-fouling layer. The antimicrobial layer formed by the second portion 142 is durable because, as noted above, the at least one nanofiber 138 is mechanically fixed to the surface portion 144 by the first portion 140 and because the poly(ethylene glycol) coating 146 is mechanically fixed to the second portion 142.

In the embodiment of FIG. 4, the second portion 142 of the nanofiber 138 can be formed as described above in reference to FIG. 3, and coated with poly(ethylene glycol) in a liquid state. In some embodiments, coating the second portion 142 with the poly(ethylene glycol) can include dipping the outer surface 124 into poly(ethylene glycol) that is in a liquid state. In other embodiments, coating the second portion 142 with the poly(ethylene glycol) can include spraying liquid poly(ethylene glycol) onto the outer surface 124.

After coating the second portion 142 with the poly (ethyhlene glycol), the poly(ethylene glycol) is cross-linked to mechanically link the poly(ethylene glycol) to the second portion 142 and form the cross-linked poly(ethylene glycol) coating 146. In some embodiments, the poly(ethylene glycol) can include a radical initiator compound that generates free radicals when exposed to energy, such as ultraviolet radiation or heat. The free radicals can initiate cross-linking of the poly(ethylene glycol). Examples of suitable UV initiator compounds include (4-bromophenyl)diphenylsulfonium triflate, (4-fluorophenyl)diphenylsulfonium triflate, (4-iodophenyl)diphenylsulfonium triflate, (4-methoxyphenyl)diphenylsulfonium triflate, (4-methylphenyl)diphenylsulfonium triflate, (4-methylthiophenyl)methyl phenyl sulfonium triflate, (4-phenoxyphenyl)diphenylsulfonium triflate, (4-phenylthiophenyl)diphenylsulfonium triflate, (4-tert-butylphenyl)diphenylsulfonium triflate, (cumene)cyclopentadienyliron(II) hexafluorophosphate, (tert-butoxycarbonylmethoxynaphthyl)-diphenylsulfonium triflate, 1-naphthyl diphenylsulfonium triflate, 2-(4-methoxystyryl)-4,6-bis(trichloromethyl)-1,3,5-triazine, bis(4-tert-butylphenyl)iodonium perfluoro-1-butanesulfonate, bis(4-tert-butylphenyl)iodonium p-toluenesulfonate, bis(4-tert-butylphenyl)iodonium triflate, boc-methoxyphenyldiphenylsulfonium triflate, diphenyliodonium hexafluorophosphate, diphenyliodonium nitrate, diphenyliodonium perfluoro-1-butanesulfonate, diphenyliodonium p-toluenesulfonate, diphenyliodonium triflate, N-hydroxy-5-norbornene-2,3-dicarboximide perfluoro-1-butanesulfonate, N-hydroxynaphthalimide triflate, triarylsulfonium hexafluoroantimonate salts, triphenylsulfonium perfluoro-1-butanesufonate, triphenylsulfonium triflate, tris(4-tert-butylphenyl)sulfonium perfluoro-1-butanesulfonate, and tris(4-tert-butylphenyl)sulfonium triflate. Examples of suitable thermal initiator compounds include azobisisobutyronitrile (AIBN), dibenzoyl peroxide, N-benzyl pyridinium bromide, N-benzyl o-cyano pyridinium bromide, N-benzyl p-cyanopyridinium bromide, N-benzyl N,N-dimethyl anilinium bromide, and benzyl triphenyl phosphonium bromide.

Thus, in some embodiments, the cross-linked poly(ethylene glycol) 146 can include a residue of a cross-linking initiator. For example, the initiator residue may include, for example, a residue of any of the ultraviolet initiators or the thermal initiators describe above.

In some embodiments, the cross-linked poly(ethylene glycol) 146 can be covalently bonded to the second portion 142 of the nanofiber 138, in addition to being mechanically fixed to the second portion 142. In such embodiments, the poly(ethylene glycol) 146 is both chemically and mechanically fixed to the second portion 142. In such embodiments, forming the antimicrobial layer can include exposing the second portion 142 and the poly(ethylene glycol) 146 to a plasma that contains argon. Free radicals formed by the argon-containing plasma produce reactive sites for covalent bonding of the poly(ethylene glycol) 146 to the second portion 142 of the at least one nanofiber 138. The argon-containing plasma does not include oxygen, as the oxygen has been found to deteriorate the nanofiber 138. In some embodiments, the argon-containing plasma can produced from a flow of argon gas at a pressure of about 250 mTorr and an applied radio-frequency power of about 200 Watts. The second portion 142 and the nanofiber 138 can be exposed to the plasma for a time ranging from about 60 seconds to about 180 seconds.

In some embodiments, the free radicals generated by exposure to the argon-containing plasma not only provide reactive sites for covalent bonding of the poly(ethylene glycol) 146 to the second portion 142, but may also provide free radicals for the cross-linking of the poly(ethylene glycol) to form the poly(ethylene glycol) coating 146. In such embodiments, there may be no need for an ultraviolet initiator or a thermal initiator, and no initiator residues present in the cross-linked poly(ethylene glycol) coating 146.

Although the embodiments described above employ poly (ethylene glycol) as the hydrophilic polymer, other suitable hydrophilic polymers can include polyvinylpyrrolidone (PVP), poly(2-methyl-2-oxazoline), poly(2-ethyl-2-oxazoline, poly(ethylene glycol) methacrylate, and hydroxypropyl cellulose.

Although the embodiments described above are directed to an antimicrobial layer formed on the outer surface 124 of the lead body 116, it is understood that the embodiments described above may also be applied to the outer surface 130 of the suture sleeve 122.

Figure 5A:
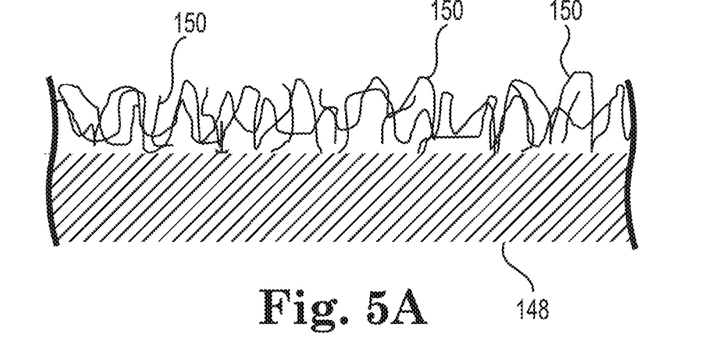
FIGS. 5A-5C are enlarged schematic cross-sectional views illustrating an antimicrobial layer and its formation on a portion of the suture sleeve of FIG. 2.
Figure 5B:
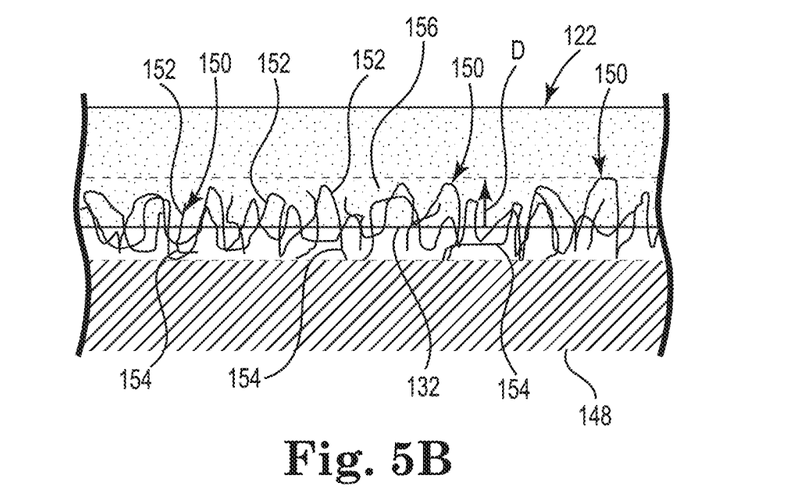
Figure 5C:
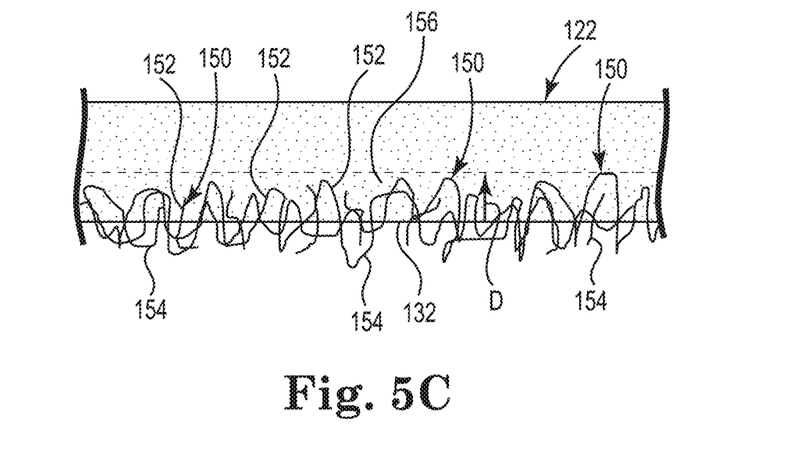

The description above in reference to FIGS. 3 and 4 described an antimicrobial layer and its formation on the outer surface 124 of the lead body 116. FIGS. 5A-5C are enlarged schematic cross-sectional views illustrating an antimicrobial layer and its formation on the inner surface 132 of the suture sleeve 122. FIG. 5A shows a core pin or mandrel 148 and at least one nanofiber 150 disposed onto the core pin or mandrel 148. The nanofiber 150 can be similar or identical to the nanofiber 138 described above in reference to FIGS. 3 and 4. The at least one nanofiber 150 can be electro-spun onto the core pin or mandrel 148. The core pin or mandrel 148 can be rotated while the nanofiber 150 is electro-spun onto the core pin or mandrel 148.

After the a least one nanofiber 150 is formed onto the core pin or mandrel 148, the nanofiber 150 and the core pin or mandrel 148 can be over-molded to form the suture sleeve 122 with inner surface 132, as shown in FIG. 5B. For example, the suture sleeve 122 can be made of silicone, in which case liquid silicone rubber is injected into a mold (not shown) containing the core pin or mandrel 148 and the nanofiber 150. The liquid silicone rubber does not fully penetrate through the nanofiber 150 to the core pin or mandrel 148 because of its relatively high viscosity and the relatively small spaces formed amongst the nanofiber 150 as it is electro spun onto the core pin or mandrel 148. Thus, the inner surface 132 is may be spaced apart from the core pin or mandrel 148. The nanofiber 150 includes a first portion 152 and a second portion 154. The first portion 152 is embedded in, or interpenetrated with, a surface portion 156 of the suture sleeve 122. The surface portion 156 extends from the inner surface 132 into the suture sleeve 122 to a depth D. The second portion 154 projects from the inner surface 132. The first portion 152 is mechanically fixed to the inner surface 132 by virtue of the embedded, interpenetrating structure.

After the silicone cross-links or cures, the core pin or mandrel 148 can be removed, as shown in FIG. 5C. As with the embodiment described above in reference to FIGS. 3 and 4, it has been found that the second portion 154 of the nanofiber 150 projecting from the inner surface 132 presents a surface morphology that is less amenable for bacterial adhesion than the inner surface 132 without the nanofiber 150. By discouraging adhesion of bacteria to the inner surface 132, the second portion 154 forms an antimicrobial layer that may inhibit bacterial colonization. The antimicrobial layer formed by the second portion 154 is durable because the nanofiber 150 is mechanically fixed to the surface portion 156 by the first portion 152.

Figure 6:
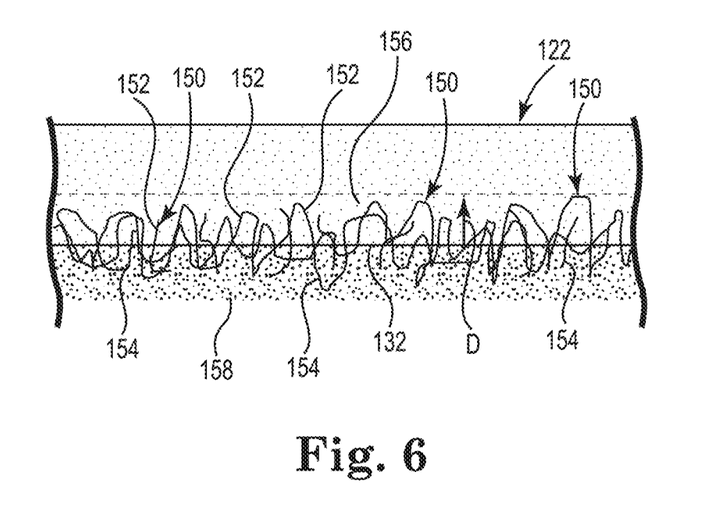
FIG. 6 is an enlarged schematic cross-sectional view of a portion of the suture sleeve of FIG. 2, illustrating an antimicrobial layer on a surface of the suture sleeve, according to some embodiments.

FIG. 6 is an enlarged schematic cross-sectional view of a portion of the inner surface 132 of the suture sleeve 122 of FIG. 2, illustrating an antimicrobial layer on a surface of an implantable device, according to some embodiments. The embodiment shown in FIG. 6 is similar or identical to the embodiment shown in FIG. 5C, except that it includes a cross-linked poly(ethylene glycol) coating 158 on the second portion 154. The poly(ethylene glycol) coating 158 is cross-linked around and between at least some of the second portion 154 so that it is mechanically linked to the at least one nanofiber 150. The poly(ethylene glycol) coating 146 is also biostable because it is cross-linked. The presence of the poly(ethylene glycol) coating 146 around the nanofiber 150 may further discourage bacterial adhesion by providing a hydrophilic, anti-fouling coating on the second portion 154 of the nanofiber 150. It has been found that the combination of the surface morphology of the second portion 154 and the hydrophilic, cross-linked poly(ethylene glycol) coating 158 provides a durable, antimicrobial, anti-fouling layer. The antimicrobial layer formed by the second portion 154 is durable because, as noted above, the at least one nanofiber 150 is mechanically fixed to the surface portion 156 by the first portion 152 and because the poly(ethylene glycol) coating 158 is mechanically fixed to the second portion 154.

In the embodiment of FIG. 6, the second portion 154 of the nanofiber 150 can be formed as described above in reference to FIGS. 5A-5C, and coated with poly(ethylene glycol) in a liquid state. In some embodiments, coating the second portion 154 with the poly(ethylene glycol) can include dipping the inner surface 132 into poly(ethylene glycol) that is in a liquid state. In other embodiments, coating the second portion 154 with the poly(ethylene glycol) can include spraying liquid poly(ethylene glycol) onto the inner surface 132.

After coating the second portion 154 with the poly (ethyhlene glycol), the poly(ethylene glycol) is cross-linked to mechanically link the poly(ethylene glycol) to the second portion 154 and form the cross-linked poly(ethylene glycol) coating 158. The poly(ethylene glycol) 158 can be cross-linked as described above for the poly(ethylene glycol) 146 in reference to FIGS. 3 and 4. Thus, in some embodiments, the cross-linked poly(ethylene glycol) 158 can include a residue of a cross-linking initiator.

In some embodiments, the cross-linked poly(ethylene glycol) 158 can be covalently bonded to the second portion 154 of the nanofiber 150, in addition to being mechanically fixed to the second portion 154. In such embodiments, the poly(ethylene glycol) 158 is both chemically and mechanically fixed to the second portion 154. In such embodiments, forming the antimicrobial layer can include exposing the second portion 154 and the poly(ethylene glycol) 158 to a plasma that contains argon. Free radicals formed by the argon-containing plasma produce reactive sites for covalent bonding of the poly(ethylene glycol) 158 to the second portion 154 of the nanofiber 150. The argon-containing plasma does not include oxygen, as the oxygen has been found to deteriorate the nanofiber 150. In some embodiments, the argon-containing plasma can produced from a flow of argon gas at a pressure of about 250 mTorr and an applied radio-frequency power of about 200 Watts. The second portion 154 and the nanofiber 150 can be exposed to the plasma for a time ranging from about 60 seconds to about 180 seconds.

In some embodiments, the free radicals generated by exposure to the argon-containing plasma not only provide reactive sites for covalent bonding of the poly(ethylene glycol) 158 to the second portion 154, but may also provide free radicals for the cross-linking of the poly(ethylene glycol) to form the poly(ethylene glycol) coating 158. In such embodiments, there may be no need for an ultraviolet initiator or a thermal initiator, and no initiator residues present in the cross-linked poly(ethylene glycol) coating 158.

Figure 7A:
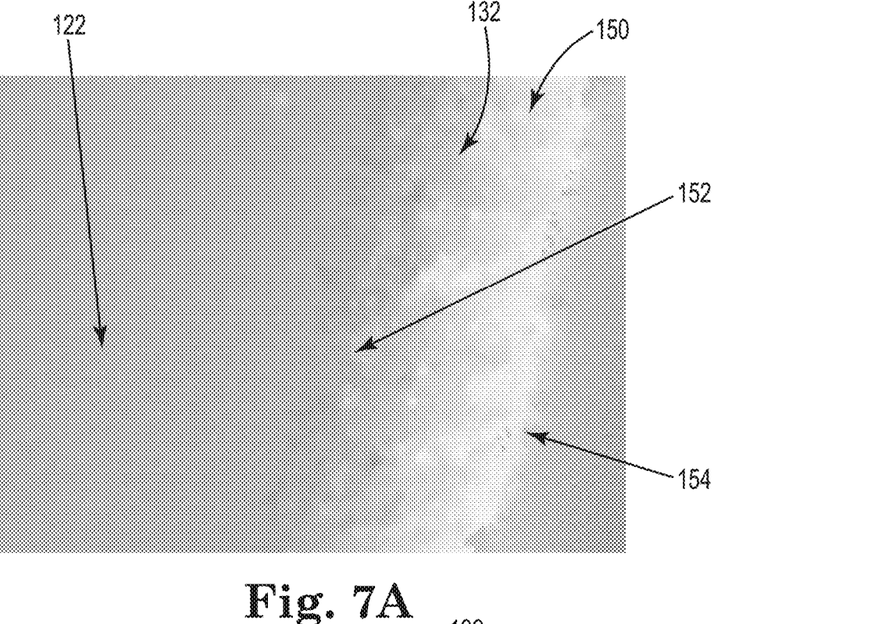
FIGS. 7A and 7B are cross-sectional micrographs of a suture sleeve illustrating an antimicrobial layer on a surface of the suture sleeve, according to embodiments.
Figure 7B:
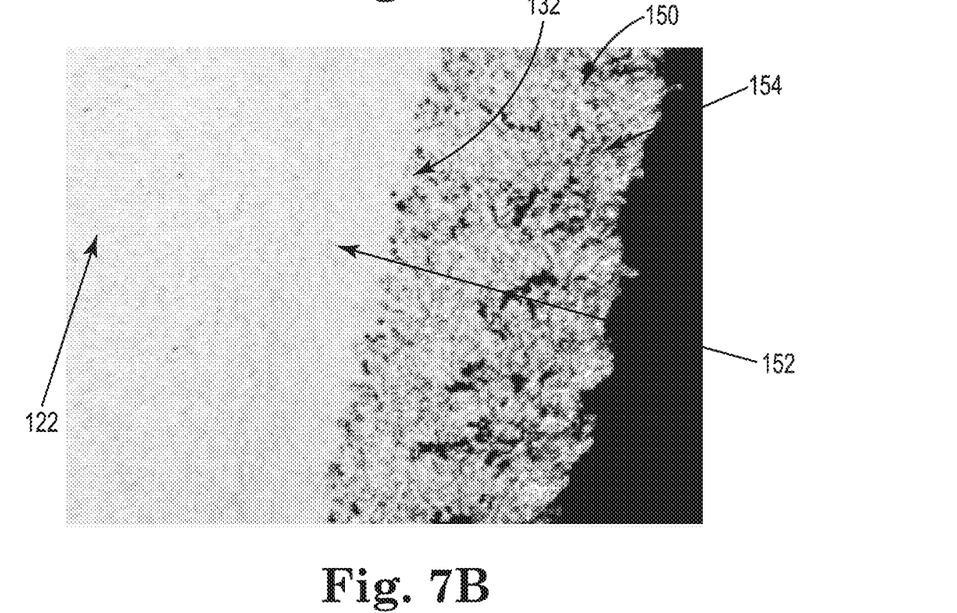

FIGS. 7A and 7B are cross-sectional micrographs of the suture sleeve 122 illustrating the inner surface 132 as well as the first portion 152 and the second portion 154 of the at least one nanofiber 150. In the example shown in FIGS. 7A and 7B, the suture sleeve 122 is made of silicone, the at least one nanofiber 150 is made of PVDF, and the second portion 154 is coated with poly(ethylene glycol) having an average molecular weight of about 400 grams/mole. FIGS. 7A and 7B are at a magnification of about 4,000×. FIG. 7A was taken under color optical illumination to more clearly show the interpenetration of the first portion 152 with the inner surface 132 of the suture sleeve 122. FIG. 7B was taken under laser illumination to more clearly show the second portion 154 projecting from the inner surface 132.

In the embodiments described above, the poly(ethylene glycol) may be a hydroxy-terminated poly(ethylene glycol). In other embodiments, the poly(ethylene glycol) may be terminated by a different functional group that may aid in cross-linking of the poly(ethylene glycol), such as a methacrylate group.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of forming an antimicrobial layer on a surface of a polymer substrate of an implantable medical device, the method comprising:

having at least one biostable nanofiber consisting of a first portion and a second portion and interpenetrating one or more loops formed from the first portion within a surface portion of the substrate, the surface portion extending from the surface into the substrate, the surface portion being in a liquid or semi-liquid state; and solidifying the surface portion, wherein the first portion of the at least one nanofiber is mechanically fixed within the surface portion and the second portion of the at least one nanofiber projects away from the surface to form a surface morphology on the surface that is antimicrobial.

2. The method of claim 1, wherein interpenetrating the first portion of the at least one nanofiber within the surface portion includes electro-spinning a nanofiber directly into the surface portion.

3. The method of claim 1, wherein interpenetrating the first portion of the at least one nanofiber within the surface portion includes:
 electro-spinning the at least one nanofiber onto a core pin or a mandrel; and
 over-molding the surface portion onto the first portion of the at least one nanofiber on the core pin or mandrel.

4. The method of claim 1, wherein solidifying the surface portion includes cross-linking the polymer substrate around the first portion of the at least one nanofiber.

5. The method of claim 1, further including:
 coating the second portion of the at least one nanofiber with a poly(ethylene glycol); and
 cross-linking the poly(ethylene glycol) coating to mechanically link the poly(ethylene glycol) to the second portion of the at least one nanofiber.

6. The method of claim 5, wherein the poly(ethylene glycol) includes at least one of an ultraviolet initiator and a thermal initiator, and cross-linking the poly(ethylene glycol) coating includes exposing the ultraviolet initiator and the thermal initiator to ultraviolet radiation or heat, respectively.

7. The method of claim 5, further including exposing the second portion of the plurality of nanofibers and the poly(ethylene glycol) coating to an argon-containing plasma to covalently bond the cross-linked poly(ethylene glycol) coating to the second portion of the plurality of nanofibers.

8. The method of claim 1, wherein the at least one nanofiber includes at least one of a fluoropolymer or a polyurethane.

9. The method of claim 1, wherein the at least one nanofiber includes poly(ethylene glycol).

10. The method of claim 1, wherein the at least one nanofiber has an average diameter ranging from about 100 nanometers to about 1,000 nanometers.

11. The method of claim 1, wherein the implantable medical device is a medical electrical lead or a suture sleeve.

* * * * *